United States Patent [19]

Stange et al.

[11] Patent Number: 5,744,042
[45] Date of Patent: Apr. 28, 1998

[54] METHOD FOR THE SEPARATION OF PROTEIN-BOUND SUBSTANCES FROM A PROTEIN-CONTAINING LIQUID BY DIALYSIS

[76] Inventors: Jan Stange, W. Seelenbiderstr. 38; Steffen Mitzner, Wendenstr. 2, both of 18055 Rostock; Wolfgang Ramlow, Goethestr. 20, D-18209 Bad Doberan, all of Germany

[21] Appl. No.: 570,816

[22] Filed: Dec. 12, 1995

Related U.S. Application Data

[63] Continuation of Ser. No. 123,002, Sep. 17, 1993, abandoned.

[51] Int. Cl.$^6$ .................................................. B01D 61/24
[52] U.S. Cl. .................... 210/645; 210/644; 210/646; 436/177; 436/178
[58] Field of Search ............................... 210/638, 644, 210/645, 646, 650, 651, 500.23, 502.1, 632; 436/177, 178; 530/362, 363, 413, 417; 435/180, 182

[56] References Cited

U.S. PATENT DOCUMENTS

| | | | |
|---|---|---|---|
| 4,163,714 | 8/1979 | Gregor | 210/651 |
| 4,352,884 | 10/1982 | Nakashima et al. | 435/180 |
| 4,375,414 | 3/1983 | Strahilevitz | 210/638 |
| 4,714,556 | 12/1987 | Ambrus et al. | 210/638 |
| 4,741,832 | 5/1988 | Leonard | 210/638 |
| 4,874,522 | 10/1989 | Okamoto et al. | 210/645 |
| 5,078,885 | 1/1992 | Matsumura | 210/638 |
| 5,167,824 | 12/1992 | Cohen et al. | 210/638 |
| 5,328,614 | 7/1994 | Matsumura | 210/638 |

*Primary Examiner*—John Kim
*Attorney, Agent, or Firm*—Dressler, Rockey, Milnamow & Katz, Ltd.

[57] ABSTRACT

The present invention provides a process of separating substances bound to a first protein in a first liquid by means of a membrane separating the first liquid from a second liquid, the process comprising the steps of: a) impregnating the membrane by passing along the membrane a solution comprising a first acceptor protein having an acceptor function for the substances to be separated; b) dialyzing the first liquid against the second liquid, the second liquid comprising a second acceptor protein having an acceptor function for the substances to be separated, wherein the membrane separating the first and second liquids contains tunnel-like structures that permit passage of the substances to be separated to the second liquid but exclude passage of the first protein and the second acceptor protein.

11 Claims, 3 Drawing Sheets

METHOD FOR THE SEPARATION OF PROTEIN-BOUND SUBSTANCES FROM A PROTEIN-CONTAINING LIQUID BY DIALYSIS

This is a continuation, of application Ser. No. 08/123,002, filed Sep. 17, 1993, now abandoned.

1. TECHNICAL FIELD

The present invention relates to membranes and membrane transport processes, and in particular to an effective method for the separation of undesired or potentially harmful protein-bound substances (PBS) and, if present, water-soluble substances (low-molecular weight and middle-molecular weight substances) and/or lipophilic substances, from a protein-containing liquid such as plasma and blood by dialysis using said membranes.

2. Background

The separation of substances which are strongly bound to a valuable protein from that protein by dialysis is impossible or at least accompanied with a number of difficulties. This is especially relevant if the protein is contained in a complex mixture such as blood or plasma.

In medicine separation techniques are widely accepted for the separation of hydrophilic toxins from blood e.g. in end stage renal disease (ESRD, uremia). Today, maintenanced hemodialysis (HD) is the live-saving long-term treatment of choice in ESRD patients if no kidney transplantation is available. However, the removal of protein-bound or lipophilic toxins remains, at present, an unsolved problem in medicine. Especially albumin-bound toxins (ABT) have been shown to be involved in the pathogenesis of different exogenous and endogenous intoxications in patients.

Thus ABTs such as butyric, valeric, caproic and caprylic acid, thyroxine and tryptophane, unconjugated bilirubin, mercaptans, digoxin-like immunoreactive substances, benzodiazepine-like substances, aromatic amino acids and phenols seem to be responsible for the induction of hepatic encephalopathy and cerebral edema in fulminant hepatic failure (FHF).

These substances are assumed to be at least partially responsible for lethal cerebral alterations seen in FHF. Moreover, FHF is typically accompanied by coagulopathy, defective ventilation, hypoxemia, pulmonary edema, electrolyte imbalance, acid-base disturbances, renal dysfunction, hypoglycemia, cardiac dysfunction, sepsis, hemorrhage leading to multiorgan failure and death. The mortality has been on an unchanged high level between 60 and 100% since years, depending on e.g. the age of the patient and the stage of encephalopathy at hospital entry.

In chronic liver insufficiency the same group of ABTs accumulates due to the insufficient metabolism of the liver in the blood and brain although the primary toxins may be different (e.g. ethanol). Therefore, symptoms such as encephalopathy normally seen in FHF may occur in these patients, too, and acute exacerbations mimicking the picture of FHF are seen frequently.

Newborn hyperbilirubinemia is another clinically relevant endogeneous intoxication. This form of hyperbilirubinemia is known to have damaging effects to the newborn brain because of the immature blood-brain barrier. Toxic effects of bilirubin in the adult human are under discussion. At least in very high concentrations the toxic effect could be clearly demonstrated.

Furthermore, there is a large number of drugs known to have a highly albumin-binding rate in cases of accidental overdosage or suicidal intoxications by e.g. tricyclic antidepressants, digoxin, digitoxin, theophylline or a benzodiazepine.

While the importance of ABT in the above-mentioned cases is generally acknowledged, there is also a significant accumulation of albumin-bound toxins in ESRD, e.g. furancarboxylic acids, indoxyl sulfate, aluminum ions, phenols and other organic acids, although patients are on regular HD treatment. The unsatisfactory search for "uremic toxins" among the "middle molecules" spectrum on the one hand and the fact that uremic plasma shows more toxic effects than its ultrafiltrate on the other hand led to the assumption that some of the "uremic toxins" may be also protein-bound.

Meanwhile this theory which has its origin as early as in 1976 has been accepted by the American Society for Artificial Internal Organs (1993) and many specialists in the USA, Europe and Japan. This indicates that not only the liver but also the kidneys take part in the separation of albumin-bound substances from the blood in order to keep them at non-toxic levels. This is already known for some drugs and indicator substances (e.g. phenol red) and has been shown recently also for furan derivatives as a special excretoric function of the kidneys which cannot adequately be replaced by hemodialysis. This explains that in dialysis patients the concentrations of these molecules reach levels which may be of pathophysiological relevance. Underlining this it has been shown that furancarboxylic acids accumulating in chronic hemodialysis patients are strong inhibitors of mitochondrial cell respiration. Furthermore, furan derivatives act as inhibitors of cell proliferation by interfering with DNA synthesis as shown in vitro.

In vivo relevant long-term complications of maintenanced HD treatment in ESRD are seen in almost every patient (e.g. dialysis-associated anemia, suppressed immune response, high infection rates, encephalopathy) that are caused by insufficiency of highly specialized or proliferative tissues (e.g. blood forming tissue). Suggesting a relation between these in vitro and in vivo results clinical investigations have shown that e.g. the grade of anemia in hemodialyzed patients strongly correlates with the plasma levels of furancarboxylic acids.

All states of disease mentioned above have in common not only the ABTs involved in the pathogenesis but also very high treatment costs for either intensive care and transplantation or long-term treatment with supplementation therapy (e.g. erythropoietin) and repeating hospital stays. Therefore, ABT-associated diseases have a considerable economic dimension with high patient numbers and treatment costs on the one hand and a bad overall prognosis leading to death or invalidity on the other hand (e.g. 400,000 patients on maintenanced HD worldwide with approximately 60 million treatments per year).

Treatment of ABT-associated diseases—State of the art

1. Dialysis and Ultrafiltration

Because of their affinity to the non-dialyzable albumin molecule ABTs are not able to permeate to a significant degree into the dialysate liquid in vitro and in vivo.

Moreover, many of these ABTs are highly lipophilic and not soluble in water.

Conventional hemodialysis effectively separates low molecular weight substances (<1500 daltons) from plasma but no protein-bound substances which are believed to be responsible for the detrimental effects of liver insufficiency.

Hemodialysis using e.g. large-pore polyacrylonitrile membranes effectively removes middle molecular weight substances (1500–5000 daltons) in addition to the low molecular weight substances but again no protein-bound substances in experimental animals; see De Groot, GH, Schalm SW, Schicht I: Large-pore hemodialytic procedures in pigs with ischemic hepatic necrosis; a randomized study, Hepatogastroenterol. Vol. 31 (1984), 254; De Groot, GH, Schalm SW, Schicht I: Comparison of large-pore membrane hemodialysis and cross-dialysis in acute hepatic insufficiency in pigs, Eur. J. Clin. Invest., Vol. 13 (1983), 65.

Therefore, dialysis and ultrafiltration are not satisfactory methods for the separation of these substances.

2. Peritoneal dialysis

Patients undergoing peritoneal dialysis (PD) as an alternative treatment lose up to 10% of the total serum albumin during a single PD session and by this way, of course, also toxic albumin-bound substances (ABT). In clinical studies typical long-term complications of HD patients, especially the above-mentioned anemia, could not be observed in PD patients. However, this enhanced removal of albumin-bound toxins by PD is accompanied by the loss of albumin which correlates with an increased mortality. Furthermore, PD is associated with a high risk of peritonitis.

3. Erythropoietin therapy

Erythropoietin therapy partially reverses the dialysis/uremia-associated anemia but is expensive. The reason for the anemia is not a lack of endogenous erythropoietin. Arterial hypertension is one of the most often seen adverse effects in this therapy.

4. Kidney transplantation

This method can ameliorate the problem of insufficient removal of ABTs in ESRD. Nevertheless, it has a number of severe complications including operation risk, intensive immunosuppression, high tumor risk. The overall life expectancy is not different from HD treatment.

5. Hemo-/Plasmaperfusion

Hemo- or plasmaperfusion over different or other adsorbents such as ion exchange resins and charcoal are also effective but not sufficiently specific. These methods also remove essential substances like hormones (corticosteroids, thyroxine) which are linked to their own transport proteins (corticosteroid transporting protein or thyroxine transporting protein).

In most of the studies made in this regard blood was perfused through sorbent columns containing charcoal or ion exchange resins. By this method protein-bound toxins were removed effectively but this was accompanied by the following disadvantages:

a) loss of blood cells, especially platelets
b) loss of clotting factors
c) activation of blood cells (platelets, leukocytes)
d) activation of the complement system
e) loss of essential plasma components blood compounds (hormones, vitamines, growth factors) due to the absolutely unspecific mode of binding
f) release of microparticles, especially when charcoal adsorbents were used.

In order to attenuate the adverse effects seen in charcoal perfusion charcoal particles are coated with different blood-compatible substances but these charcoal adsorbents exhibit a decreased ability to bind protein-bound substances. Hemoperfusion over micro-encapsulated charcoal effectively removes low-molecular weight substances (<1500 daltons) from plasma but no protein-bound substances which are believed to be responsible for the detrimental effects of liver insufficiency.

Of all extracorporeal dialysis and adsorption techniques especially hemoperfusion over an albumin-coated resin (e.g. Amberlite XAD-7) or agarose beads to which albumin had been covalently linked have been shown to effectively remove bilirubin and other toxic protein-bound organic anions from the blood of experimental animals (Wilson R. A., Webster K. H., Hofmann A. F.: Toward an artificial liver: in vitro removal of unbound and protein-bound plasma compounds related to hepatic failure, Gastroenterol., Vol. 62 (1972), 1191.; Scharschmidt B. F., Plotz P. H., Berk P. D.: Removing substances from blood by affinity chromatography. II. Removing bilirubin from blood of jaundiced rats by hemoperfusion over albumin-conjugated agarose beads, J. Clin. Invest., Vol. 53 (1974), 786. No assessment was made concerning the selectivity or possible adverse effects of this method.

However, these albumin-coated adsorbents did not remove low and middle molecular weight substances (Zakim and Boyer (ed.), Hepatology. A textbook of liver disease, W. B. Saunders Company, 1990, p. 479–482).

In conclusion hemo- or plasma-perfusion remain an unselective method.

6. Plasma exchange

In this method the plasma of the patient is separated from blood by filtration or by centrifugation and is replaced by an albumin solution or plasma. This procedure shows the following disadvantages:

a) most protein-bound toxins are not only distributed in plasma but also in tissues. After a plasma exchange session a redistribution of the toxins into the purified plasma occurs. This was accompanied with the clinical observation that patients in FHF undergoing this treatment awoke from coma but only for the time of treatment and fell back into deep coma after the end of treatment. Thus, plasma exchange had to be done frequently to be effective, which led to typical immunological reactions mentioned below.

b) the observed immunological reactions arising from frequent plasma exchange have been known for a long time from blood transfusions as allergic reactions up to anaphylactoid reactions. A special manifestation was described as the "transfusion lung".

c) the risk of viral infection is present (HIV, hepatitis).

d) in FHF the organism answers the massive cell degradation with an increased secretion of growth hormones in order to enhance organ regeneration. These growth hormon levels are higher than in healthy persons and are therefore not present in the donor plasma.

e) plasma exchange is expensive.

7. Exchange transfusions

In severe newborn-hyperbilirubinemia today exchange transfusions are the treatment method of choice. The therapy is helpful to the patient because irreversible brain damage is prevented. However, the transfusions have similar disadvantages as mentioned above for plasma exchange.

8. Other extracorporeal methods

Different other approaches especially towards the field of FHF treatment and with respect to the removal of protein-bound toxins have been made in the past years:

a) charcoal-impregnated hollow fibers/dialysis against sorbent suspensions

Trials to combine the hemocompatibility of dialysis with the effectivity of charcoal adsorption by filling charcoal into cellulosic membranes or recirculate adsorbent suspensions (powdered charcoal and ion exchange resins) in order to remove "middle molecules" did not at all or not sufficiently come up to the expectations. Especially the removal of strongly protein-bound fractions of ABT (e.g. unconjugated bilirubin) was insufficient. The reasons for this, in our opinion, was the use of membranes which lack the predispositions for the "tunneling effect" which will be described below.

b) lipophilic liquid membranes

A further effort was made to remove protein-bound toxins by the use of hydrophobic semipermeable polymer membranes filled with lipophilic liquids enabling the passage of water-insoluble compounds like middle-molecular weight fatty acids and mercaptans. An alkaline dialysate (pH 13) solution was proposed as acceptor solution for these toxins. The disadvantages of this method are the following:

1. Some of the ABTs are insoluble in this liquid membrane and are therefore excluded from the removal process (e.g. unconjugated bilirubin).
2. The insolubility of hydrophilic toxins (e.g. ammonia) in the liquid phase excluded their removal, too, and required the additional use of a further dialysis procedure, because most of the above described intoxications were of complex nature including hydrophilic and hydrophobic toxins. By the use of an additional dialysis device the extracorporeal blood volume as well as blood-polymer contact increases. Last but not least costs are very high.
3. The use of alkaline dialysate solutions might be of potential harm to the patient influencing the endogenous pH value at least in cases of membrane damage.

9. Biohybrid systems

These systems are bioreactors designed for the processing of blood or plasma which include biological components (e.g. liver slices, liver cells) which will provide a natural detoxification. Because of the limited functionality and short life of liver slices only cell-based systems are acceptable. The disadvantages of this method are:

a) there is no stable and save source providing sufficient amounts of cells needed for the treatment.

The most important cell for the detoxification of protein-bound toxins, the hepatocyte of the liver until today could not be produced by cultivation in vitro without genetic manipulation which is followed by cell alteration and therefore connected with further risks that cannot be calculated. The use of tumor liver cells which could be produced by in vitro cultivation is connected with the risk of developing tumor and furthermore with risks arising from an metabolic alteration of the cells which cannot be foreseen. The use of animal cells is connected with immunological reactions between the plasma/blood of the patient on the one hand and the xenogenic liver cell on the other.

b) difficulty of the method

Because of the poor possibilities for cryoconservation of the cells or complete bioreactors the preparation of the device has to be done always just prior to use. This makes this method usable only for highly specialized centers.

c) high costs

All steps of this treatment involve high costs.

10. Liver transplantation

Today this is the method of choice in patients with either chronic or acute end stage liver failure because it shows the best long time survival rates from all therapies mentioned for liver failure. The limiting factors of this method are limited availability of suitable donor organs (long waiting lists), surgery risk, life-long immune suppressive therapy to avoid rejection associated with the common complications (e.g. high infection risk, high tumor risk, risk of diabetes).

Moreover, the indications for transplantation are very tight, automatically excluding a large number of fatally ill patients. Thus, transplantation did not avoid the need for sufficient detoxification procedures for those patients not eligible for surgery. A number of those patients eligible for surgery is in a status too bad to undergo surgery because of FHF with coma, hypotension, high bleeding risk. These patients are in need for a sufficient "liver bridging treatment" to prepare for transplantation and, in a number of cases, when patients come into FHF after transplantation it is needed again. Last but not least transplantation causes high costs arising from surgery as well as from the immune supressive therapy.

Therefore, it would be useful to provide a method for the separation of protein-bound substances such as ABTs from protein-containing liquids, e.g. from blood or plasma of patients suffering e.g. from FHF, chronic liver insufficiency, accidental or suicidal drug overdosage and ESRD, which is effective, safe and less expensive. It would be advantageous if this method did not interfere with the homeostasis of the liquid, e.g. blood, for instance, by undesired removal of valuable components, e.g. proteins, from the liquid or addition of potentially harmful (toxic) substances to the liquid.

Thus, one object of the present invention is to provide a method for the separation of protein-bound substances from a protein-containing liquid containing these substances by dialysis. Another object of the invention is to provide a membrane for the separation of said protein-bound substances from a protein-containing liquid containing these substances by dialysis.

Further objects will become apparent from the following description, drawings and claims.

SUMMARY OF THE INVENTION

The invention is based on the unexpected finding that protein-bound substances (PBS), including even those being strongly bound, can be removed from protein-containing liquids (A) by dialysis against a dialysate liquid (B) and by means of a semipermeable membrane and by means of a protein having an acceptor function for the PBS.

Preferably, the dialysate liquid (B) of the present invention contains a protein having an acceptor function for the protein-bound substance (PBS) to be removed from the protein-containing liquid (A), in general of the type of protein present in the PBS-protein complex in liquid (A).

In case of plasma or blood as protein-containing liquid (A) the preferred acceptor protein in the dialysate liquid (B) is albumin, in particular human serum albumin or recombinant human albumin.

The membrane of the present invention preferably comprises two functionally different parts. One part has the actual separating membrane function permitting the PBS and, if present, the water-soluble substances to pass through under the conditions of the process of the present invention and excluding the protein(s) which had bound the PBS in liquid (A) and the acceptor protein of liquid (B), and the other part has a port- and adsorption function. Preferably, the membrane is coated with a protein having an acceptor function for the PBS. In a preferred embodiment the membrane of the present invention comprises a tunnel-like structure facing the liquid (A) side, the tunnels having a length less than about 10 μm and having a diameter sufficiently small to exclude the protein in liquid (A), and a port- and adsorption-structure on the dialysate liquid (B) side. Preferably, the membrane is coated on at least one side, preferably the dialysate liquid (B) side, with a thin film of a protein having an acceptor function for the protein-bound substances.

The membrane of the present invention may have the macroscopic form of a flat film, a thin-walled but large diameter tube, or preferably fine hollow fibers. Membrane technology, hollow-fiber membranes, and dialysis is described in Kirk-Othmer, Encyclopedia of Chemical Technology, third edition, Vol. 7 (1979), 564–579, in particular 574–577, Vol. 12 (1980), 492–517 and Vol. 15 (1981), 92–131. Furthermore, membranes and membrane separation processes are described in Ullmann's Encyclopedia of Industrial Chemistry, Fifth edition, Vol A 16 (1990), 187–263.

The matrix material for the membrane may be made from many materials, including ceramics, graphite, metals, metal oxides, and polymers, as long as they have an affinity towards the protein on the liquid (A) and the dialysate liquid (B). The methods used most widely today are sintering of powders, stretching of films, irradiation and etching of films and phase inversion techniques. The preferred materials for the membranes of the present invention are organic polymers selected from the group consisting of polysulfones, polyamides, polycarbonates, polyesters, acrylonitrile polymers, vinyl alcohol polymers, acrylate polymers, methacrylate polymers, and cellulose acetate polymers. Especially preferred are polysulfone membranes hydrophilized with e.g. polyvinylpyrrolidone.

A precise and complete definition of a membrane is rather difficult; see Ullmann, loc. cit., page 190–191, No. 2.1 and 2.2. A membrane can be homogeneous, microporous, or heterogeneous, symmetric or asymmetric in structure. It may be neutral, or may have functional groups with specific binding or complexing abilities. The most important membranes currently employed in separation processes are the asymmetric membranes; see Ullmann, loc. cit., page 219 et seq., No. 4.2. Known asymmetric membranes have a "finger"-type structure, a sponge-type structure with a graded pore size distribution or a sponge type structure with a uniform pore size distribution; see Ullmann, loc. cit., page 223–224.

The most preferred membrane structure of the present invention is an asymmetric membrane composed of a thin selective skin layer of a highly porous substructure, with pores penetrating the membrane more or less perpendicularly in the form of fingers or channels from the skin downward. The very thin skin represents the actual membrane and may contain pores. The porous substructure serves as a support for the skin layer and permits the protein having an acceptor function to come close to the skin and to accept the protein-bound substances penetrating the skin from the liquid (A) side towards the dialysate liquid (B) side.

Prior to the separation procedure the membrane is preferably prepared as follows. The membrane is treated from the liquid (A) side and/or from the liquid (B) side with a liquid which contains the protein having an acceptor function, preferably a 0.9% NaCl solution, containing the acceptor protein, preferably human serum albumin in a concentration from about 1 to about 50 g/100 ml, more preferably from about 5 to about 20 g/100 ml. The treatment time is about 1 to about 30 min, preferably about 10 to about 20 min, at a temperature from about 15° to about 40° C., preferably from about 18° to about 37° C.

The method of the present invention for the separation of protein-bound substances and, of course conventional water-soluble substances that may be present, from a protein containing liquid (A) is carried out as follows:

The liquid (A) to be purified is passed through a dialyzer comprising a membrane along the liquid (A) side of the membrane with a flow rate of about 50 to about 500 ml/min, preferably about 100 to about 200 ml/min per one sqm membrane area on the liquid (A) side. The dialysate liquid (B) is passed along the dialysate liquid (B) side of the membrane with a flow rate of about 50 to about 500 ml/min, preferably of about 100 to about 200 ml/min per one sqm membrane area and preferably with the same flow rate as the liquid (A).

The dialysate liquid (B) obtained and containing the protein-bound substances and possibly water-soluble substances from liquid (A) preferably is then passed through a second conventional dialyzer that is connected to a conventional dialysis machine. A dialysis against an aqueous standard dialysate is carried out. By this dialysis water-soluble substances are exchanged between the dialysate liquid (B) and the standard dialysate. Thus, water-soluble toxins such as urea or creatinine can be separated from the dialysate liquid (B) and electrolytes, glucose and pH can be balanced in the dialysate liquid (B) and, therefore, also in liquid (A). The dialysate liquid (B) obtained freed from water-soluble substances preferably is then passed through a charcoal-adsorbent, e.g. Adsorba 300 C from GAMBRO AB or N350 from ASAHI, and an anion exchange column, e.g. BR350 from ASAHI, to remove the protein-bound substances from the protein acceptor in the dialysate liquid (B). The purified dialysate liquid (B) obtained is then returned to the dialysate liquid (B) side of the membrane of the present invention and reused.

Other advantages and benefits will be apparent to those skilled in the art from the detailed description that follows.

Figure 1:
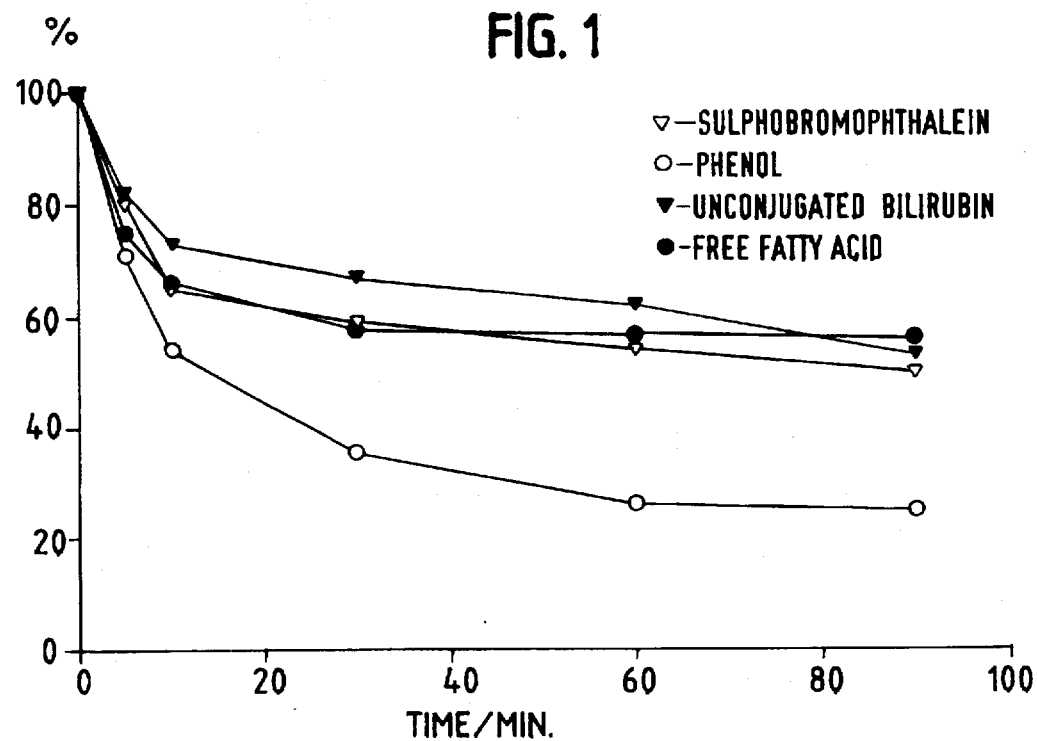
FIG. 1 is a graph showing the results of an in vitro separation of protein-bound substances (unconjugated bilirubin, free fatty acids, phenol, sulfobromophthalein) from plasma (liquid (A)) in accordance with the method of the present invention. The decrease of the protein-bound substances (PBS) is shown in percent of the initial concentrations in the plasma (liquid (A)).
Figure 2:
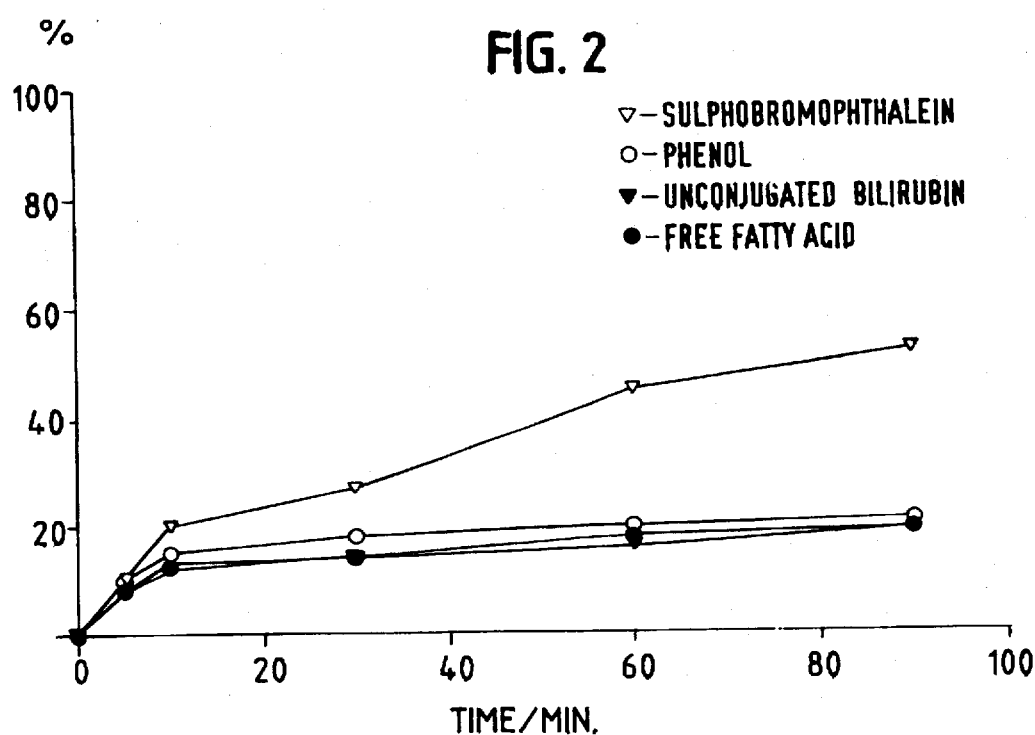
FIG. 2 is a graph showing the increase of protein-bound substances in dialysate solution (liquid (B); corresponding to FIG. 1 and obtained from the same experiment) in percent of the initial concentrations in the plasma (liquid (A)).
Figure 3:
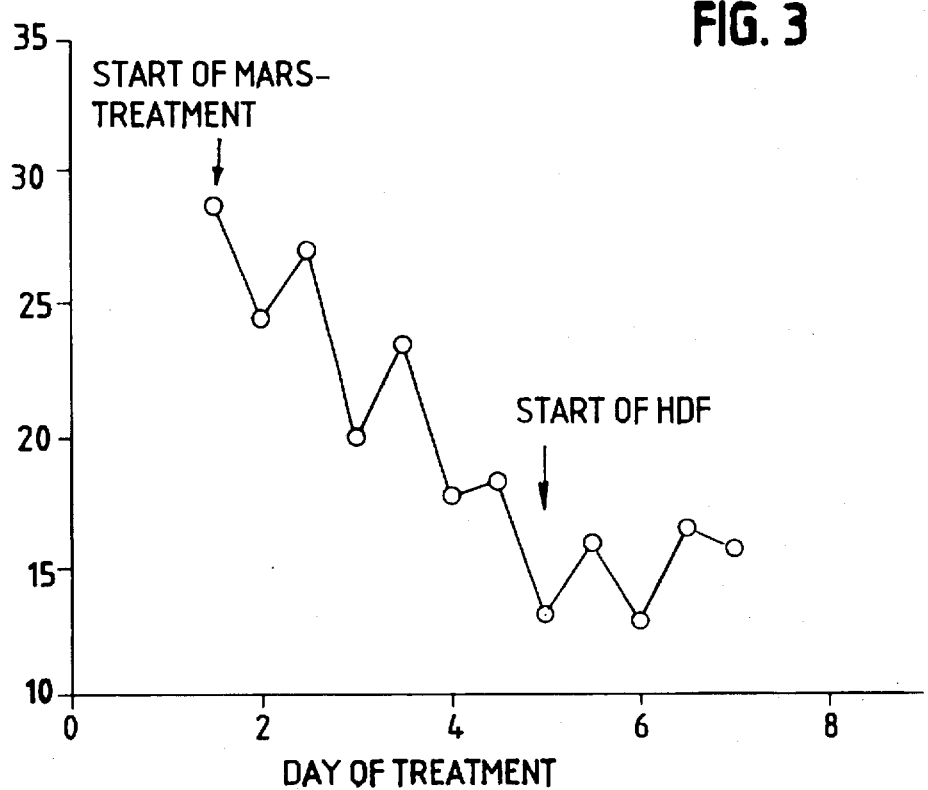
FIG. 3 is a graph showing total serum bilirubin concentrations in a 29 year old patient with an acute exacerbation of a chronic liver insufficiency during a 4 days period of MARS treatment followed by a 2 days conventional HDF.
Figure 4:
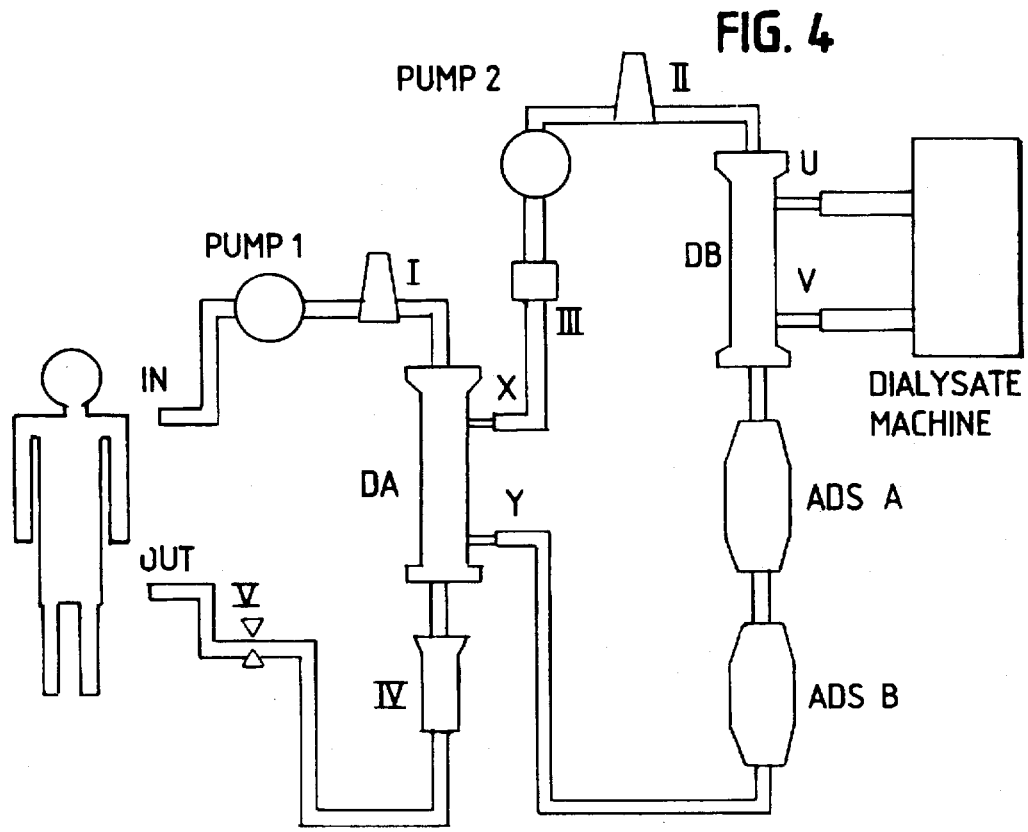
FIG. 4, 5 and 6 illustrate embodiments for the purification of blood by means of hemodialysis according to the present invention.
Figure 5:
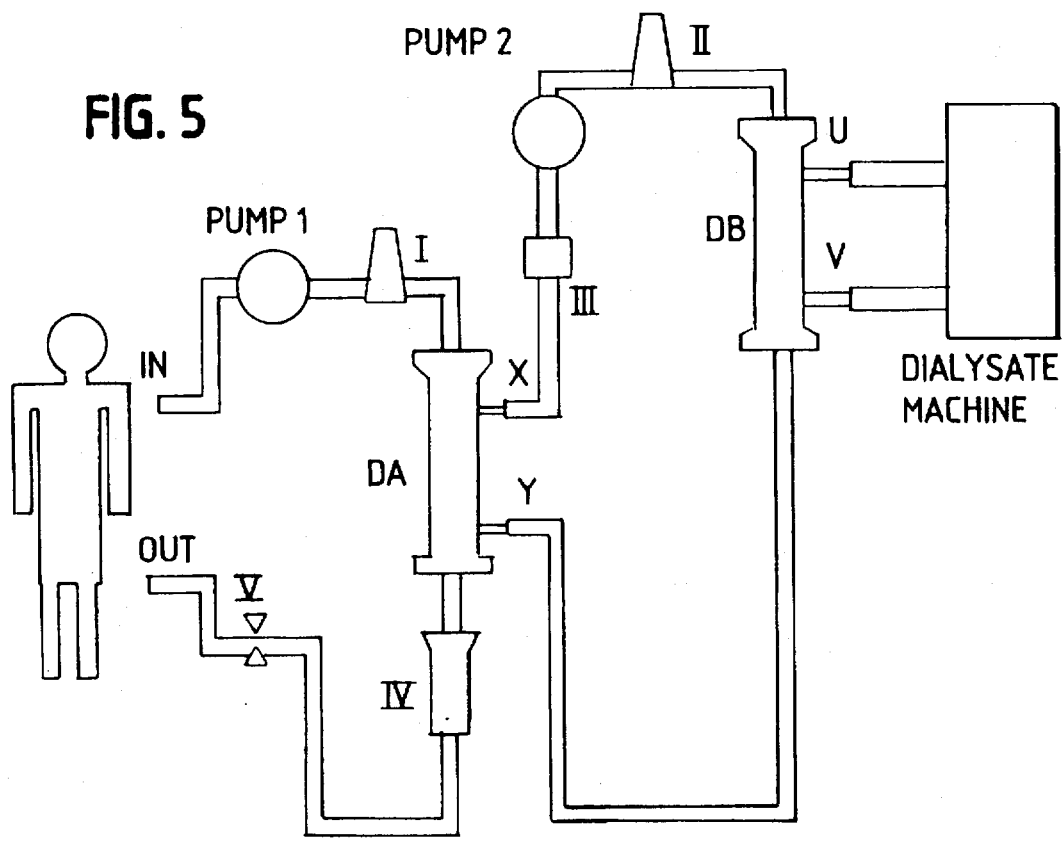
Figure 6:
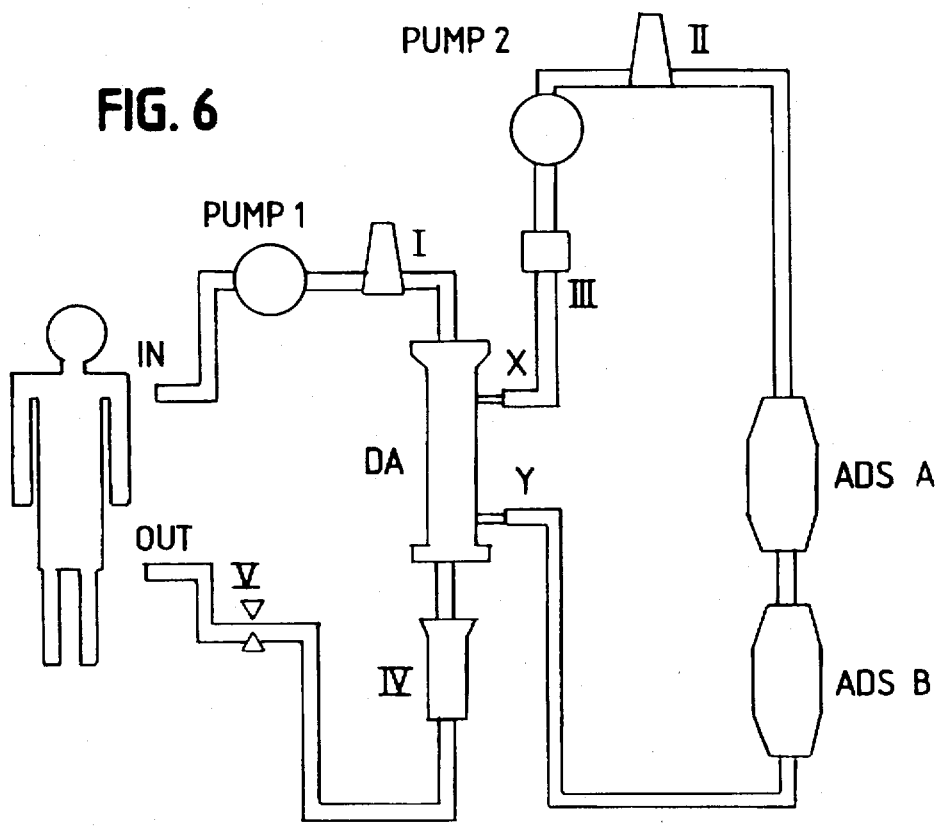

| DA | Dialyzer A (albumin coated Membrane) |
|---|---|
| DB | Dialyzer B (conventional dialyzer) |
| ADS A | Adsorbent A |
| ADS B | Adsorbent B |
| Pump 1 | Blood roller pump |
| Pump 2 | first albumin dialysate roller pump |
| Pump 3 | second albumin dialysate roller pump |
| I–V | Safety devices: |
| I | Blood line bubble snare |
| II | Albumin dialysate line bubble snare |
| III | Blood lack detector |
| IV | Veneous drop chamber |
| V | Safety clamp |
| in/out | Blood inflow and outflow |
| X/Y | Albumin dialysate flow connectors (DA) |
| U/V | Conventional dialysate flow connectors (DB) |

The blood (liquid (A)) flows from "in" pumped by pump 1 through the bubble snare into the dialyzer (DA) and after passing it through the veneous drop chamber, after that passing the safety clamp. Safety devices are not part of the invention but have to be used because of safety regulations. The albumin dialysate (liquid (B)) is pumped by roller pump 2 from connector X in direction to connector Y or from Y to X, but preferably counter-currently to the blood flow, passing at first the blood lack detector (III) and also a bubble snare (II). Thereafter, liquid (B) passes a conventional dialyzer (DB) and, if desired, adsorbent columns (A and B).

Other possibilities are:

The liquid (B) is only passed through adsorbents and not through a dialyzer

The liquid (B) passes only through dialyzer DB and not through adsorbents.

The conventional dialyzer (DB) is connected to a conventional dialysate liquid which may be coming from a conventional dialysis machine or pumped by other perfusor or roller pumps from bags.

DETAILED DESCRIPTION OF THE INVENTION

A. Method for separating protein-bound substances from protein-containing liquids The present invention provides a practical and effective method for the removal of undesired or potentially harmful protein-bound substances and/or lipophilic substances from protein-containing liquids such as plasma and blood.

The basic procedure is similiar to conventional high flux dialysis with modifications according to the present invention as described below.

1. The dialysate liquid (B)

The dialysate liquid (B) contains a protein serving as an acceptor for the protein-bound substances (PBS) to be removed from the liquid (A). The acceptor protein should have a sufficient affinity towards the substances which are bound to the protein in liquid (A). A preferred acceptor protein is human serum albumin. The concentration of the acceptor protein is from about 1 to about 50 g/100 ml, preferably from about 6 to about 40 g/100 ml, more preferably from about 8 to about 30 g/100 ml and most preferably from about 8 to about 20 g/100 ml.

The dialysate liquid (B) contains furthermore salts like NaCl, KCl, $MgCl_2$, $CaCl_2$, sodium lactate and glucose monohydrate in amounts depending on the electrolyte composition in the blood of the specific patient. For example, in the dialysis of a patient suffering hypopotassemia a higher concentration of potassium ions is required.

Preferred ion concentrations in a dialysate liquid (B) that is bicarbonate buffered are for sodium from about 130 to about 145 mmol/1000 ml, for calcium from about 1.0 to about 2.5 mmol/1000 ml, for potassium from about 2.0 to about 4.0 mmol/1000 ml, for magnesium from about 0.2 to about 0.8 mmol/1000 ml, for chloride from about 100 to about 110 mmol/1000 ml, for bicarbonate from about 30 to about 40 mmol/1000 ml, for acetate from about 2 to about 10 mmol/1000 ml, for human serum albumin from about 1 to about 50 g/100 ml, preferably from about 6 to about 40 g/100 ml, more preferably from about 8 to about 30 g/100 ml, and most preferably from about 8 to about 20 g/100 ml.

More preferred ion concentrations in a dialysate liquid (B) that is bicarbonate buffered are for sodium from about 135 to about 140 mmol/1000 ml, for calcium from about 1.5 to about 2.0 mmol/1000 ml, for potassium from about 3.0 to about 3.5 mmol/1000 ml, for magnesium from about 0.4 to about 0.6 mmol/1000 ml, for chloride from about 104 to about 108 mmol/1000 ml, for bicarbonate from about 34 to about 38 mmol/1000 ml, for acetate from about 4 to about 8 mmol/1000 ml, for human serum albumin from about 1 to about 50 g/100 ml, preferably from about 6 to about 40 g/100 ml, more preferably from about 8 to about 30 g/100 ml, and most preferably from about 8 to about 20 g/100 ml.

Preferred ion concentrations in a dialysate liquid (B) that is acetate buffered are for sodium from about 130 to about 145 mmol/1000 ml, for calcium from about 1.0 to about 2.5 mmol/1000 ml, for potassium from about 2.0 to about 4.0 mmol/1000 ml, for magnesium from about 0.2 to about 0.8 mmol/1000 ml, for chloride from about 100 to about 110 mmol/1000 ml, for acetate from about 30 to about 40 mmol/1000 ml, for human serum albumin from about 1 to about 50 g/100 ml, preferably from about 6 to about 40 g/100 ml, more preferably from about 8 to about 30 g/100 ml, and most preferably from about 8 to about 20 g/100 ml.

More preferred ion concentrations in a dialysate liquid (B) that is acetate buffered are for sodium from about 135 to about 140 mmol/1000 ml, for calcium from about 1.5 to about 2.0 mmol/1000 ml, for potassium from about 3.0 to about 3.5 mmol/1000 ml, for magnesium from about 0.4 to about 0.6 mmol/1000 ml, for chloride from about 104 to about 108 mmol/1000 ml, for acetate from about 33 to about 38 mmol/1000 ml, for human serum albumin from about 1 to about 50 g/100 ml, preferably from about 6 to about 40 g/100 ml, more preferably from about 8 to about 30 g/100 ml, and most preferably from about 8 to about 20 g/100 ml.

An example for a dialysate liquid (B) comprises from about 10 to about 20% by weight human serum albumin, about 6.1 g NaCl, about 4.0 g sodium lactate, about 0.15 g KCl, about 0.31 g $CaCl_2 \times 2\ H_2O$, 0.15 g $MgCl_2 \times 6\ H_2O$, and 1.65 g glucose monohydrate per liter of dialysate liquid (B).

2. The membrane

The membrane of the present invention preferably comprises two functionally different parts (regions). One part has the actual separating membrane function permitting the PBS and the water-soluble substances to pass through under the conditions of the process of the present invention and excluding the protein(s) which had bound the PBS in liquid (A) and the acceptor protein of liquid (B), and the other part has a port- and adsorption function. Preferably, the membrane is coated with a protein having an acceptor function for the PBS. In a preferred embodiment the membrane of the present invention comprises a thin layer of a tunnel-like structure facing the liquid (A) side, the tunnels having a length less than about 10 µm, preferably less than about 5 µm, more preferably less than about 0.1 µm and most preferably between about 0.01 and about 0.1 µm. The tunnels have a diameter sufficiently small to exclude the protein in liquid (A), preferably to permit the passage of molecules having a molecular weight from about 20,000 daltons to about 66,000 daltons, more preferably from about 50,000 to about 66,000 daltons through the tunnels. Preferably the sieve coefficient of the membrane with respect to the protein in liquid (A) is less than 0.1, more preferably less than 0.01. Furthermore, the membrane preferably comprises a port- and adsorption-structure on the dialysate liquid (B) side. This part has to provide a structure sufficiently open to permit the acceptor protein in the dialysate liquid (B) to enter the port- and adsorption layer to accept the PBS coming from the liquid (A) side of the membrane. Moreover the internal surface of this part acts as an adsorber for the PBS via the acceptor protein that is adsorbed by the coating procedure described in the following or by other structures suitable for binding the PBS. This adsorption can either be stable over time or reversible. Preferably the membrane is coated on at least one side with a thin film of a protein having an acceptor function for the protein-bound substances. A commercial dialyzer comprising a membrane of the present invention may contain on the liquid (B) side a solution of the acceptor protein.

The membrane of the present invention may have the macroscopic form of a flat film, a thin-walled but large diameter tube, or preferably fine hollow fibers.

The matrix material for the membrane may be made from various materials, including ceramics, graphite, metals, metal oxides, and polymers, as long as they have an affinity towards the protein on the liquid (A) and the dialysate liquid (B). The methods used most widely today are sintering of powders, stretching of films, irradiation and etching of films and phase inversion techniques. The preferred materials for the membranes of the present invention are organic polymers selected from the group consisting of polysulfones, polyamides, polycarbonates, polyesters, acrylonitrile polymers, vinyl alcohol polymers, acrylate polymers, methacrylate polymers, and cellulose acetate polymers.

The preferred polymer membranes used in the present invention are highly permeable asymmetric polysulfone membranes hydrophilized with e.g. polyvinylpyrrolidone, e.g. HF 80 of Fresenius AG.

Such membranes and membrane modules, dialysis cardriges, artificial kidney membrane systems are commercially available for instance from Fresenius AG, Polyflux from GAMBRO AB, CT190G from Baxter Inc.

First part: The layer or structure of the membrane facing the liquid (A) side has to provide the actual membrane permitting a selective transfer of protein-bound substances and water-soluble substances, i.e. low-molecular substances and "middle molecules" from the liquid (A) side to the dialyzing solution (liquid (B) side). Thus, an effective net transport of undesired substances occurs from the liquid (A) side to the dialysate liquid (B) side following the concentration gradient for the undesired substances decreasing from the liquid (A) side towards the dialysate liquid (B) side. Three conditions have to be met for the actual membrane:

1. The tunnels have to be sufficiently short, preferably less than about 5 μm, more preferably less than about 1 μm, and most preferably less than about 0.1 μm.
2. The tunnel diameter has to be sufficiently large to permit passage of the undesired molecules and sufficiently small to inhibit passage of the desired molecules contained in liquid (A) towards liquid (B) and of the acceptor protein from liquid (B) to liquid (A). In case of plasma or blood as liquid (A) the exclusion limit is preferably about 66,000 daltons. Preferably the sieve coefficient of the membrane with respect to the protein in liquid (A) is less than 0.1, more preferably less than 0.01.
3. The chemical, physical etc. structure of the layer or structure of the actual membrane facing the liquid (A) side is such that passage of the undesired substances is permitted, e.g. by hydrophobic and hydrophilic microdomains.

Second part: The layer or structure of the membrane facing the liquid (B) side has to provide a more open membrane structure normally in a sponge- or finger-like fashion. This part provides an important port- and adsorption-function within this part of the membrane:

1. Due to the open-spaced structure of this part of the membrane the acceptor protein coming from the dialysate liquid (B) side can approach the dialysate side ostium of the structure facing the liquid (A) side described above and accept undesired substances, such as protein-bound substances passing through the tunnel-like structure from the liquid (A) side.
2. Due to the large total surface area present in this structure it adsorbs remarkable amounts of the protein-bound substances (PBS) via attached molecules that function as a kind of spacer in this mediate membrane adsorption or the PBS are directly membrane bound if the membrane has a capacity to adsorb the PBS due to its own structure. This adsorption can either be reversible or irreversible but preferably it is reversible.
3. Due to the open structure towards the dialysate liquid (B) side of the membrane a dialysate movement that might be directed perpendicular or in parallel to the outer membrane surface or in a different fashion can transport acceptor protein molecules both into the port layer and out of the port layer. Preferably the movement and the transport perpendicular to the outer membrane surface is provided by an alternating influx and outflux movement of liquid (B) that moves into the port membrane and back out into the liquid (B) stream. This influx and outflux can be provided by a pulse-like pressure profile obtained by the use of roller pumps or a change in transmembranal pressure changing along the membrane from being directed towards the liquid (B) first (positive TMP) and to the liquid (A) at last (negative TMP); TMP=transmembranal pressure.

Thus, the dialysis membrane of the present invention preferably is functionally divided into a tunnel-like part and a finger- or sponge-like port/adsorption part. Both of them have to fullfill certain prerequisites to render the method of the present invention possible. The ideal tunnel-like part would be one with a length next to zero (0.01 to 0.1 μm), a diameter next to the size of the desired protein to be purified and kept in the retentate, e.g. the diameter of albumin. In other words, the tunnel-like part should have a diameter sufficiently small to retain valuable and desired substances of the liquid (A) in the retentate and to permit protein-bound substances and other undesired substances contained in liquid (A) to pass to the dialysate liquid (B) side.

The ideal port/adsorption part of the dialysis membrane of the present invention has a very open structure to enable the acceptor protein to approach and leave the area next to the dialysate side of the tunnel. It has a large inner surface which adsorbs the PBS directly or via the attached acceptor protein. The total diameter of this part should again be as small as possible to render the exchange into the dialysate stream more effective. The latter two points can be brought to their extremes almost excluding the other one according to whether more adsorption or more transit through the port/adsorption part of the membrane is desired.

Conventional dialysis membranes for purifying e.g. plasma or blood can be classified by functional or structural criteria. Functional criteria are high flux, low flux or highly permeable, whereas structural criteria are e.g. flat, hollow fiber, symmetric or asymmetric. The group of tunnel-like membranes (TM) useful for the present invention is not sufficiently described by these terms because a) TM are high flux and highly permeable membranes but not every high flux membrane named "highly permeable" is a TM (e.g. AN69 from HOSPAL);
b) TM can be asymmetric but not every asymmetric membrane is a TM (e.g. F8 from FRESENIUS AG);
c) TM can be asymmetric and highly permeable but not every asymmetric and highly permeable membrane is a TM (PMMA from Toray)
d) TM can be symmetric but not every symmetric membrane is a TM (e.g. Cuprophan from AKZO).

Therefore the term tunnel-like membrane represents a new quality of structural and functional features of dialysis membranes useful for the present invention.

4. Pretreatment and conditions of the membrane

The membrane of the present invention preferably is pretreated as follows. The membrane is impregnated on at least one side, preferably both from the liquid (A) side and from the liquid (B) side with a solution of the acceptor protein. A preferred solution for the impregnating step is a 0.9% NaCl solution, containing the acceptor protein, preferably human serum albumin, in a concentration from about 1 to about 50 g/100 ml, preferably from about 6 to about 40 g/100 ml, more preferably from about 8 to about 30 g/100 ml, and most preferably from about 8 to about 20 g/100 ml. The impregnating solution is passed along the liquid (A) side and the liquid (B) side of the membrane for a time sufficient to permit penetration and adsorption of the acceptor protein on the two parts of the membrane, in general from about 1 to about 120 min, preferably from about 10 to about 60 min, at a temperature from about 15° to about 40° C., preferably from about 18° to about 37° C., the pH value being from about 5 to about 9, preferably about 7. The pretreatment can be carried out immediately prior to use of the membrane, but the pretreated membrane may also be stored under sterile conditions at a temperature up to 24° C. for up to two years if the acceptor protein is human serum albumin. Preferably the impregnating solution is pumped by roller pumps exhibiting a "pulse like pressure profile" during the coating procedure, e.g. by two roller pumps, one on the dialysate side compartment and one on the blood side compartment of the dialyzer. Preferably there is a phase delay between the pressure profiles of the two pumps thus to ensure an effective in- and outflow of the solution on both sides of the membrane.

5. Procedure for the separation of protein-bound substances (PBS) from a protein containing liquid (A)

The procedure for the separation of PBS from a protein-containing liquid (A) preferably is carried out as follows: Liquid (A) to be purified is passed along the liquid (A) side of the dialysis membrane of the present invention with a flow rate from about 50 to about 300 ml/min, preferably from about 100 to about 200 ml/min per sqm of the dialysis membrane. The dialysate liquid (B) is passed along the dialysate side (B) of the membrane with a flow rate from about 50 to about 1000 ml/min, preferably from about 100 to about 500 ml/min per sqm of the dialysis membrane. The flow rates of the liquid (A) and thus liquid (B) are preferably in the same order of magnitude. The ratio of the flow rate of liquid (A) to liquid (B) is from about 1:0.1 to about 1:10, preferably from about 1:1 to about 1:5. The retentate is the purified protein-containing liquid (A) from which protein-bound substances and other undesired substances are removed.

In a preferred embodiment of the process of the present invention the first dialysis step of the liquid (A) is combined with two steps of aftertreatment of the dialysate liquid (B) obtained.

First the dialysate liquid (B) obtained is passed through a second conventional dialyzer which is connected to a conventional dialysis machine. Dialysis is carried out against an aqueous standard dialysate liquid. By this dialysis water-soluble substances can be exchanged between the dialysate liquid (B) and a standard dialysate liquid.

Water-soluble toxins, urea and/or creatinine are removed from the dialysate liquid (B), and electrolytes, glucose and the pH value can be balanced in the dialysate liquid (B) which is the retentate. The dialysate liquid (B) is thereafter passed through a charcoal-adsorbent, e.g. Adsorba 300 C from GAMBRO AB or N350 from ASAHI, and then through an anion exchange column, e.g. BR350 from ASAHI, to remove the protein-bound substances from the acceptor protein in the dialysate liquid (B). The purified acceptor protein-containing dialysate liquid (B) is then returned to the liquid (B) side of the membrane of the present invention.

This procedure has been tested experimentally for the separation of albumin-bound drugs and toxins in a protein-containing liquid and led to a significant reduction of these compounds in the liquid.

Other possible simplified embodiments of the procedure of the present invention comprise the following modifications. The dialysate liquid (B) coming from the dialyzer may be passed through another dialyzer but not through any adsorbent. The dialysate liquid (B) coming from the dialyzer may be passed through one or two adsorbents but not through another dialyzer. The dialysate liquid (B) coming from the dialyzer may be pumped directly back into the inlet of the dialysate compartment of the dialyzer (e.g. by a roller pump) thus realizing a sufficient movement of the dialysate liquid (B) and sufficient removal of ABT. A further simple modfication would be a dialyzer with a dialysate compartment filled with the dialysate liquid (B) comprising human serum albumin in a concentration of from about 1 to about 50 g/dl, preferably from about 6 to about 40 g/dl, more preferably between 8 and 30 g/dl, and most preferably from about 8 to about 20 g/dl that is closed at the dialysate inlet and outlet. The whole dialyzer may be moved, e.g. by shaking or rolling.

The benefit of the method of the present invention is that a biological protein-containing liquid such as blood or plasma contaminated with potentially harmful or undesired protein-bound substances and possibly undesired water-soluble substances can be selectively purified by the method of this invention so that the biological liquid contains the protein-bound substance and the other undesired substances in a lower concentration than before and does not exhibit the potentially harmful or unwanted effects which it had prior to the dialysis treatment.

Another benefit of the method of the present invention is that the chemical and physical homeostasis of the biological liquid remains almost unchanged, i.e. the method and the dialysis membrane used for it exert good biocompatibilty.

The method of the present invention furthermore has the advantage that it is simple, practical and suitable for treating large volumes of biological liquids, e.g. blood in an extracorporeal circuit repeatedly for hours and for different conditions with commercially available dialysis machines.

A disposable set for the separation of protein-bound substances and water-soluble substances from plasma or blood containing said substances can comprise a membrane as described before, a second conventional dialyzer for hemodialysis, a conventional charcoal adsorber unit for hemoperfusion, and a conventional ion exchange resin unit for hemoperfusion interconnected by tubing and a unit of a human serum albumin containing dialysate liquid.

A disposable set for the separation of protein-bound substances and water-soluble substances from plasma or blood containing said substances may as well comprise a dialyzer having a membrane as described before and being filled on the dialysate liquid (B) side with a human serum albumin containing liquid, a second conventional dialyzer for hemodialysis, a conventional charcoal adsorber unit for hemoperfusion, and a conventional ion exchange resin unit for hemoperfusion interconnected by tubing and a unit of a human serum albumin containing dialysate liquid.

B. Evaluation of removal of PBS and water soluble substances

All compounds were determined immediately after the experiment in order to avoid degradation especially of the light instable bilirubin.

Bromosulfophthalein: Spectrophotometrically according to the method of BECH

Bilirubin: a) Spectrophotometrically according to the method of JENDRASSIK; b) KODAK EKTACHEM dry chemistry. Both methods showed good correlation in the range of concentrations used.

Phenols: a) Spectrophotometrically according to the method of BECHER; b) HPLC. Again both methods showed good correlation in the range of concentrations used.

Free fatty acids according to the method of LAURELL and TIBBLING (i.e. fatty acids that have not formed esters)

Digoxin: ABBOTT analyzer/dry chemistry

Digitoxin: ABBOTT analyzer/dry chemistry creatinine, urea, uric acid, transaminases, blood cell counts: KODAK EKTACHEM dry chemistry.

C. The in vitro model

A conventional dialysis machine with two closed loop compartments (a plasma compartment and a compartment for dialysis solution) is used in order to permit the measurement not only of the decreasing concentrations in the biological liquid but also the increasing concentrations in the dialysate which is the essential criterion to distinguish a membrane transport process from an adsorption to the membrane. Two glas bottles about 25 cm high and about 10 cm diameter with a volume of 500 ml each are used, one as container for the biological liquid containing plasma the other as container for the dialysate solution. Both bottles are have connectors for two tubes, one for the inflow and one for the outflow of plasma or dialysate respectively. The distance between the inflow and the outflow should not be smaller than 10 cm in order to avoid "shunt circulation". The two connectors of each bottle are connected with two flexible plastic tubes (about 100 cm and about 6 mm diameter) each with a silicone segment permitting the use of a conventional roller pump for dialysis. The other end of the two tubes from the bottle containing the plasma are connected with the connectors of the blood side of a dialysator in the following manner: the outflow of the bottle is connected with the inflow of the dialysator, the outflow of the dialysator is connected with the inflow of the bottle. The other end of the two tubes from the bottle containing the dialysate are connected with the connectors of the dialysate side of the dialysator in the following manner: The outflow of the bottle is connected with the dialysate inflow of the dialysator and the dialysate outflow of the dialysator is connected with the inflow of the bottle. The plasma inflow of the dialysator is placed next to the dialysate outflow in order to design the dialysate flow through the dialysator countercurrently to the plasma flow as it is known from clinical hemodialysis. The silicone segments of the inflow/outflow tubes of the plasma bottle are used to pump the plasma by a simultane roller pump. The silicone segments of the inflow/outflow tubes of the dialysate bottle are used to pump the dialysate by a simultane roller pump also. In this way the inflow/outflow volumes of both compartments are balanced and transmembranal water losses which could influence the results are avoided.

Preparation of the plasma used for in vitro experiments a) For evaluation of the method of the present invention using a polysulfone dialysis membrane Human heparinized plasma was taken from young male donors and enriched with model substances with a high protein binding rate:

—caprylic acid (750 mg/1000 ml)

—phenol (530 mg/1000 ml)

—unconjugated bilirubin (11 mg/100 ml)

—sulfobromophthalein (230 mg/1000 ml)

110 mg unconjugated bilirubin, 230 mg sulfobromophthalein, 750 mg caprylic acid, and 530 mg phenol were dissolved in 50 ml of a 0.1M NaOH solution. Thereafter 2.5 g human albumin (fatty acid free, SIGMA) were dissolved in the solution. Thereafter the pH value was adjusted to 7.4 by addition of a 30 percent acetic acid solution. Thereafter this toxin cocktail was mixed with 950 ml heparinized plasma. 500 ml of this plasma solution were filled into the plasma bottle.

Composition of the dialysate: 100 ml of a 20 percent (20 g/100 ml) human albumin solution were mixed with 400 ml of a commercial CVVH dialysis solution. 500 ml of this albumin containing solution were filled into the dialysate bottle.

b) For evaluation of other dialysis membranes/hemofilters

Human heparinized plasma was taken from young male donors and enriched with model substances with a high protein-binding rate:

—unconjugated bilirubin (11 mg/100 ml)

—sulfobromophtaleine (230 mg/1000 ml)

as well as with model substances wich are known as markers of uremia and effectivity of dialysis:

—creatinine (6 mg/100 ml)

—urea (100 mg/100 ml)

—uric acid (17 mg/100 ml)

110 mg unconjugated bilirubin, 230 mg sulfobromophthalein, 60 mg creatinine, 1000 mg urea, and 170 mg uric acid were dissolved in 50 ml of a 0.1M NaOH solution. Thereafter 2.5 g human albumin (fatty acid free, SIGMA) were dissolved in the solution. Thereafter the pH value was adjusted to 7.4 by addition of a 30 percent acetic acid solution at room temperature. Thereafter this toxin cocktail was mixed with 950 ml heparinized human plasma. 500 ml of this plasma solution were filled into the plasma bottle.

After filling the bottles they were closed hermetically and the pump segments (inflow and outflow) installed to the simultane roller pumps in a manner permitting recirculation of each (plasma and dialysate) circle counter-currently. The flow rates were adjusted at 100 ml/min. The temperature was adjusted to 37° C.

The following dialysis membranes/hemofilters were used:

a) For the evaluation of the principle of the method of the present invention

HF 80, FRESENIUS AG, Germany b) For the evaluation of other dialysis membranes

Diafilter 30, AMICON, U.S.A.

FH 88, GAMBRO AB, Sweden

LUNDIA PRO 5, GAMBRO AB, Sweden

CT 110 G, BAXTER, U.S.A.

SPAN, ORGANON TECHNIKA, Netherlands

KF 201 EVAL N 13, KAWASUMI, Japan

B1-2.1U, TORAY Medical Co., Japan

FILTRAL 16, HOSPAL, France

Dialysis membranes, technical information from the firms

*The highly permeable FRESENIUS AG polysulfone membrane is a asymmetric membrane with a 0.5 to 1 µm skin layer determining the cut off (about 40,000 daltons). The skin layer is supported by a macroporous support layer of about 40 µm thickness for the High flux dialysis membrane and of about 35 µm thickness for the hemofiltration membrane. The hydrophobic surface structure of the polysulfone membrane is hydrophilized by polyvinylpyrrolidone.

The low permeable FRESENIUS AG polysulfone hollow fiber membrane is a asymmetric membrane with a 0.5 to 1 µm skin layer determining the cut off (ca 5000 daltons) which is supported by a macroporous support layer of about 40 µm thickness. The hydrophobic surface structure of the polysulfone membrane is hydrophilized by polyvinylpyrrolidone. These fibers are present in the following Fresenius dialyzers: F3, F4, F5, F6, F7, F8.

*The HOSPAL PAN membrane (AN 69) is a symmetric membrane based on polyacrylonitrile with a high permeability and a membrane thickness of 50 µm. This membrane is present in Filtral 8–20 as a hollow fiber and in Biospal.

*The ORGANON TECHNIKA SPAN membrane is an asymmetric membrane based on polyacrylonitrile.

*The DIAFILTER is an asymmetric hollow fiber polysulfone hemofilter membrane with a skin layer determining the cut off supported by a macroporous support layer. This hemofiltration membrane is present in the following AMICON filters: Minifilter, Minifilter plus, Diafilter 10, 20, 30, and 50.

*The Lundia pro 5 membrane is a flat polycarbonate dialysis membrane.

*The GAMBRO AB polyamide hollow fiber membranes are asymmetric membranes sold in three modifications:

Polyamide for high flux dialysis and hemodiafiltration with a wall thickness of 50 µm, designed as a 3-layer and of high hydrophobicity. The internal diameter of the hollow fiber is 220 µm. These hollow fibers are present in Polyflux 130 and Polyflux 150 (Trademark names).

Polyamide for hemofiltration with a wall thickness of 60 µm, designed as a 3-layer and of a high hydrophilicity. The internal diameter of the hollow fiber is 215 µm. These hollow fibers are present in FH 22, FH 77, FH 88 and with a wall thickness of 50 µm in FH 66 (Trademark names).

Polyamide for water ultrafiltration (for the separation of pyrogens) with a wall thickness of 60 µm designed as a "finger structure" of lower hydrophilicity. The internal diameter of the hollow fiber is 215 µm. These hollow fibers are present in U 2000 and U 7000 (Trademark names).

*The KF 201 EVAL N13 is a ethylene-vinyl alcohol copolymer hollow fiber membrane with a wall thickness of 32 µm. This membrane is also present in KF 101 EVAL N16.

*The TORAY PMMA hollow fiber membrane is an asymmetric membrane on the basis of polymethylmethacrylate with a wall thickness of 30 µm in B1-1.6U and B1-2.1U or of 20 µm in B2-0.5 up to B2-2.0 and B1-0.6H up to B1-1.6H.

*The BAXTER CT 100 G is a cellulose triacetate hollow fiber membrane. It has been described as a hybrid cellulose material with a symmetric pore size distribution and a wall thickness of 15 µm. This type of hollow fibers is also present in BAXTER CT 190 G.

Each dialyzer was impregnated before its use by preperfusion with a human serum albumin solution (5 g/100 ml) on the blood side as well as on the dialysate side with a flow rate of 50 ml/min for a period of 20 min.

Abbrevations in the tables:

| | |
|---|---|
| Alb. | Albumin |
| Un. Bil. | unconjugated Bilirubin |
| c. Bil. | conjugated Bilirubin |
| SBP | Sulphobromophtalein |
| Ph | Phenol |
| FFA | Free fatty acid, in this case caprylic acid |
| DIG | Digitoxin |
| Crea | Creatinine |
| Ur. acid | Uric acid |

D. In vitro Results a) Evaluation of the Principle

Tab. 1 Removal of PBS from plasma (liquid A) in vitro (HF 80, Fresenius AG), plasma concentrations (in liquid A):

| Time (min) | Alb. (g/dl) | Un. Bil. (mg/dl) | SBP (mg/l) | Ph (mg/l) | FFA (mg/l) |
|---|---|---|---|---|---|
| 0 | 3.5 | 11.70 | 230 | 529 | 749 |
| 5 | 3.4 | 9.36 | 186 | 370 | 562 |
| 10 | 3.4 | 8.42 | 151 | 291 | 502 |
| 30 | 3.4 | 7.72 | 133 | 190 | 434 |
| 60 | 3.4 | 7.02 | 124 | 137 | 419 |
| 90 | 3.3 | 5.85 | 117 | 127 | 412 |

In order to demonstrate the importance of the albumin in the dialysate liquid (B) a comparative test was performed under the same conditions as in Tab. 1 but omitting the albumin in the dialysate liquid (B). The results are shown in Comparative Tab.1.

Comparative Tab. 1. Removal of PBS from plasma (liquid A) in vitro (HF 80, Fresenius AG), plasma concentrations (in liquid A) using a conventional dialysate liquid without albumin:

| Time (min) | Alb. (g/dl) | Un. Bil. (mg/dl) | SBP (mg/l) | Ph (mg/l) | FFA (mg/l) |
|---|---|---|---|---|---|
| 0 | 3.5 | 11.70 | 230 | 529 | 749 |
| 5 | 3.4 | 11.5 | 227 | 420 | 730 |
| 10 | 3.4 | 11.42 | 221 | 371 | 723 |
| 30 | 3.4 | 11.44 | 218 | 290 | 719 |
| 60 | 3.4 | 11.39 | 211 | 270 | 718 |
| 90 | 3.3 | 11.40 | 215 | 268 | 724 |

Tab. 2. Removal of PBS from plasma (Liquid A) (HF 80, Fresenius AG), dialysate concentrations (in liquid B)

| Time (min) | Alb. (g/dl) | Un. Bil. (mg/dl) | SBP (mg/l) | Ph (mg/l) | FFA (mg/l) |
|---|---|---|---|---|---|
| 0 | 4.0 | 0.00 | 0 | 0 | 0 |
| 5 | 3.0 | 0.9 | 21 | 52 | 149 |
| 10 | 3.1 | 1.5 | 48 | 79 | 187 |
| 30 | 2.9 | 1.7 | 67 | 100 | 202 |
| 60 | 2.9 | 2.1 | 103 | 111 | 217 |
| 90 | 2.8 | 2.3 | 119 | 116 | 224 |

A comparative test was performed under the same conditions as in Tab. 2 but omitting the albumin in the dialysate liquid (B). The results are shown in Comparative Tab.2.

Comparative Tab. 2. Removal of PBS from plasma (Liquid A) (HF 80, Fresenius AG), dialysate concentrations (in liquid B) using a conventional dialysate liquid without albumin:

| Time (min) | Alb. (g/dl) | Un. Bil. (mg/dl) | SBP (mg/l) | Ph (mg/l) | FFA (mg/l) |
|---|---|---|---|---|---|
| 0 | 0.0 | 0.0 | 0 | 0 | 0 |
| 5 | <0.2 | 0.0 | 0 | 28 | 0 |
| 10 | <0.2 | 0.0 | 0 | 79 | 0 |
| 30 | <0.2 | 0.0 | 0 | 121 | 0 |
| 60 | <0.2 | 0.0 | 0 | 173 | 0 |
| 90 | <0.2 | 0.0 | 0 | 181 | 0 | b) From Different Types of Dialyzers/Membranes

Tab. 3. In vitro removal of PBS and hydrophilic toxins from plasma (liquid A) (Amicon Diafilter), plasma concentrations (liquid A).

| time (min) | Alb (g/dl) | SBP (mg/l) | Un. Bil. (mg/dl) | c. Bil. (mg/dl) | Crea (mg/dl) | Urea (mg/dl) | Ur. acid (mg/dl) |
|---|---|---|---|---|---|---|---|
| 0 | 3.5 | 230 | 11.7 | 0.6 | 6.8 | 120 | 16.8 |
| 30 | 3.4 | 86 | 4.5 | 0.47 | 3.2 | 37 | 9.8 |
| 60 | 3.3 | 56 | 3.9 | 0.40 | 2.9 | 37 | 8.1 |

Tab. 4. In vitro removal of PBS and hydrophilic toxins from plasma (liquid A) (Amicon Diafilter), dialysate concentrations (liquid B).

| time (min) | Alb (g/dl) | SBP (mg/l) | Un. Bil. (mg/dl) | c. Bil. (mg/dl) | Crea (mg/dl) | Urea (mg/dl) | Ur. acid (mg/dl) |
|---|---|---|---|---|---|---|---|
| 0 | 4.0 | 0 | 0.00 | 0.00 | 0.0 | 0 | 0.0 |
| 30 | 3.3 | 9 | 0.46 | 0.14 | 3.6 | 47 | 10.3 |
| 60 | 3.3 | 44 | 0.91 | 0.36 | 3.5 | 47 | 10.3 |

Tab. 5. In vitro removal of PBS and hydrophilic toxins from plasma (liquid A) (FH 88 from GAMBRO). plasma concentrations (liquid A).

| time (min) | Alb (g/dl) | SBP (mg/l) | Un. Bil. (mg/dl) | c. Bil. (mg/dl) | Crea (mg/dl) | Urea (mg/dl) | Ur. acid (mg/dl) |
|---|---|---|---|---|---|---|---|
| 0 | 3.5 | 230 | 11.7 | 0.6 | 6.8 | 120 | 16.8 |
| 30 | 3.2 | 47 | 7.3 | 0.13 | 2.8 | 19 | 3.0 |
| 60 | 3.1 | 32 | 6.3 | 0.13 | 2.7 | 12 | 3.0 |

Tab. 6. In vitro removal of PBS and hydrophilic toxins from plasma (liquid A) (FH 88 from GAMBRO), Dialysate concentrations (liquid B).

| time (min) | Alb (g/dl) | SBP (mg/l) | Un. Bil. (mg/dl) | c. Bil. (mg/dl) | Crea (mg/dl) | Urea (mg/dl) | Ur. acid (mg/dl) |
|---|---|---|---|---|---|---|---|
| 0 | 4.0 | 0 | 0.00 | 0.00 | 0.0 | 0 | 0.0 |
| 30 | 3.5 | 33 | 1.08 | 0.07 | 3.5 | 30 | 6.9 |
| 60 | 3.3 | 49 | 1.68 | 0.12 | 3.4 | 28 | 6.9 |

Tab. 7. In vitro removal of PBS and hydrophilic toxins from plasma (liquid A) (CT 100 G from BAXTER), plasma concentrations (liquid A).

| time (min) | Alb (g/dl) | SBP (mg/l) | Un. Bil. (mg/dl) | c. Bil. (mg/dl) | Crea (mg/dl) | Urea (mg/dl) | Ur. acid (mg/dl) |
|---|---|---|---|---|---|---|---|
| 0 | 3.4 | 232 | 11.7 | 0.6 | 6.8 | 120 | 16.8 |
| 30 | 3.3 | 114 | 8.8 | 0.5 | 3.0 | 29 | 8.2 |
| 60 | 3.2 | 84 | 7.6 | 0.45 | 3.0 | 38 | 8.3 |

Tab. 8. In vitro removal of PBS and hydrophilic toxins from plasma (liquid A) (CT 110 G from BAXTER), Dialysate concentrations (liquid B).

| time (min) | Alb (g/dl) | SBP (mg/l) | Un. Bil. (mg/dl) | c. Bil. (mg/dl) | Crea (mg/dl) | Urea (mg/dl) | Ur. acid (mg/dl) |
|---|---|---|---|---|---|---|---|
| 0 | 4.0 | 0 | 0.00 | 0.00 | 0.0 | 0 | 0.0 |
| 30 | 3.5 | 59 | 0.8 | 0.02 | 3.0 | 39 | 8.1 |
| 60 | 3.3 | 84 | 1.1 | 0.02 | 3.0 | 38 | 8.1 |

Tab. 9. In vitro removal of PBS and hydrophilic toxins from plasma (liquid A) (SPAN from Organon Technika), Plasma concentrations liquid A).

| time (min) | Alb (g/dl) | SBP (mg/l) | Un. Bil. (mg/dl) | c. Bil. (mg/dl) | Crea (mg/dl) | Urea (mg/dl) | Ur. acid (mg/dl) |
|---|---|---|---|---|---|---|---|
| 0 | 3.5 | 240 | 11.7 | 0.6 | 6.8 | 120 | 16.8 |
| 30 | 3.2 | 167 | 9.2 | 0.58 | 27 | 38 | 6 |
| 60 | 3.2 | 148 | 8.6 | 0.58 | 2.5 | 38 | 6 |

Tab. 10. In vitro removal of PBS and hydrophilic toxins from plasma (liquid A) (span von Organon Technika), Dialysate concentrations (liquid B).

| time (min) | Alb (g/dl) | SBP (mg/l) | Un. Bil. (mg/dl) | c. Bil. (mg/dl) | Crea (mg/dl) | Urea (mg/dl) | Ur. acid (mg/dl) |
|---|---|---|---|---|---|---|---|
| 0 | 4.0 | 0 | 0.00 | 0.00 | 0.0 | 0 | 0.0 |
| 30 | 3.6 | 6 | 0.19 | 0.17 | 2.6 | 38 | 7.0 |
| 60 | 3.6 | 18 | 0.19 | 0.18 | 2.6 | 38 | 7.0 | c) Influence of Different Albumin Concentrations in the Dialysate Liquid (B)

Phenol-enriched plasma: Human heparinized plasma was taken from young male donors and enriched with phenol. This was performed by dissolving 530 mg phenol in 50 ml of a 0.1M NaOH solution. Thereafter 2.5 g human albumin (fatty acid free, SIGMA) were added. Thereafter the pH value was adjusted to 7.4 with a 30 percentage acetate solution. Finally this toxin cocktail was mixed with 950 ml pooled plasma from healthy young male donors. 500 ml of this plasma solution were filled into the plasma bottle on the plasma side of a dialyzer.

Dialysate liquid (B):200 ml of a 20 percent (20 g/100 ml) human albumin solution were mixed with 300 ml of a commercial CVVH dialysis solution. 500 ml of this solution (i.e. 80 g/l albumin) were filled into the dialysate bottle on the dialysate side of a dialyzer.

After filling the bottles they were closed hermetically and the pump segments (inflow and outflow) installed to the simultane roller pumps in a manner enabeling recirculation of each (plasma and dialysate) circle counter currently. The flow rates were adjusted to 100 ml/min. The temperature was adjusted to 37° C.

Tab. 11. Removal of phenol from plasma (liquid A) in vitro (HF 80, FRESENIUS AG) with enhanced albumin concentration in the dialysate (8 g/dl), plasma and dialysate concentrations

| time | Phenol concentration (mg/l) | |
|---|---|---|
| (min) | liquid A (plasma) | liquid B (dialysate) |
| 0.0 | 529 | 0 |
| 2.5 | 158 | 148 |
| 5.0 | 132 | 151 |
| 10.0 | 116 | 148 |
| 20.0 | 105 | 147 |

E. In vivo System

A commercial dialysis machine (A 2008, Fresenius) was chosen as hardware equipment for the in vivo system. Every single piece was commercially available and had safety approval from the German Federal Health Authority, Berlin, for usage in a extracorporeal therapeutic blood treatment.

The blood pump of the A 2008 was used to supply continuous blood flow of 160 ml/min through an asymmetric polysulfone hollow fiber dialyzer (1.8 sqm, HF 80, Fresenius), that was on both sides albumin impregnated as described above. The liquid (B) dialysate compartment was a closed loop system which contained 1000 ml of Ringers lactate solution with albumin in a concentration of 5 g/100 ml (i.e. a concentration used for intravenuous infusions or liquid replacement in plasma exchange). The flow rate of this albumin containing liquid (B) dialysate of 120 ml/min was realized by the second pump of the machine (normally used for substitution liquids). Moreover, the in vitro-system was modified by introducing a three-step regeneration of the albumin-containing liquid (B) dialysate, thus increasing the PBS-separation capacity and adding the possibility of effective hemofiltration and separation of water soluble toxins.

The liquid (B) dialysate loop contained in this order:

1. An additional conventional large pore dialyzer (1.3 sqm polysulfon hollow fiber dialyzer, HF 60, FRESENIUS AG) which was connected to the normal dialysate compartment of the A 2008. While the albumin-containing closed-loop liquid (B) dialysate was passed through the blood compartment of the dialyzer, a standard bicarbonate dialysate (potassium ions 4 mmol/liter) was employed on the other side. The aim of this first step was to remove water-soluble factors of hepatic coma (ammonia, imbalanced amino acids, conjugated bilirubin etc.) to support electrolyte-, glucose- and pH-regulation and to support or replace kidney function in hepatorenal syndrome or other types of kidney failure.

2. A commercial column of activated charcoal (Adsorba 300C, GAMBRO AB). The aim of this second step was to remove a first group of PBS (e.g. aromatics, fatty acids) from the albumin in order to facilitate the reuse of the albumin solution in the closed-loop system.

3. A commercial anion exchange resin (Plasorba BR-350, Asahi Medical). The aim of this third step was the separation of unconjugated bilirubin and accumulated bile acids from the albumin solution.

After this regeneration the albumin solution was recirculated into the liquid (B) dialysate compartment of the HF 80 dialyzer for further blood purification.

F. In vivo Results

*Patient 1

The patient was a 30 year old Caucasian woman with an acute decompensation of a chronic liver failure after a six year history of alcoholism. The patient was treated for 10 days conservatively without success. At entry to the treatment the patient was in grade IV hepatic encephalopathy (i.e. deep coma, patient not reacting to painful stimuli). Hypotension, hypoglycemia and alcalosis were present.

Biochemistry: thromboplastine time (Quick) 19%, activated coagulation time was higher than 200 seconds, anti-thrombine III was 18%, platelet count was $73 \times 10^9$/liter (with an decreasing tendency). The total bilirubin was 615 µmol/liter, unconjugated bilirubin 51 µmol/liter, cholinesterase 16 µmol/liter, ammonia 96 µmol/liter. The amount of aminotransferases was five to tenfold increased, the blood pH was 7.5. The patient underwent three treatment procedures (on three subsequent days) with treatment times from about 7 and ten hours per day using a detoxification system as described below.

No adverse reactions were observed during the treatment. Blood pressure, oxygen saturation, blood glucose level and blood pH improved slowly but continuously.

During the treatment the patient recovered from unconciousness and fully awoke after the second treatment without remaining neurological symptoms of encephalopathy (no flapping tremor, fully orientated, no delay in communicational and physical response, recovery of normal reflexes). During the following days the activity of liver enzymes decreased slowly to 50%, the thromboplastine time increased to 40%. Within three following days the platelet count increased up to $130 \times 10^9$/liter and antithrombine III to 43%.

Tab. 12. Patient 1: Total serum bilirubin levels pre- and post-treatment

| | | Total serum bilirubin | | |
|---|---|---|---|---|
| No. of treatment | time of treatment (h) | before treatment (mg/dl) | after treatment (mg/dl) | Total decrease (mg/dl) |
| 1 | 7 | 36 | 25.3 | 10.7 |
| 2 | 10 | 34.5 | 23.2 | 11.3 |
| 3 | 8 | 23.5 | 17.5 | 6.1 |

Tab. 13. Patient 1: Unconjugated serum bilirubin levels pre- and post-treatment

| | | Total serum bilirubin | | |
|---|---|---|---|---|
| No. of treatment | time of treatment (h) | before treatment (mg/dl) | after treatment (mg/dl) | Total decrease (mg/dl) |
| 1 | 7 | 3.0 | 2.5 | 0.5 |
| 2 | 10 | 3.3 | 2.3 | 1.0 |
| 3 | 8 | 1.8 | 1.7 | 0.1 |

Patient 2 male, 34 years old, chronic alcoholic liver disease

The patient (120 kg bodyweight) was known as alcoholic for six years and admitted to the hospital for slowly increasing jaundice accompanied by signs of infection (fever, high white blood cell counts, left shift), loss of appetite and impairment of general status. He was treated for three weeks conservatively. As the general status worsened rapidly under conservative treatment and serum bilirubin concentrations rose to levels up to 37.7 mg/100 ml the patient was treated with the MARS method. During five days of treatment no further worsening of the general status of the patient did occur. Treatment time of four hours obviously was too short for the patient. On day 4 a short 2 hour MARS treatment was combined with a two hours hemodiafiltration. The very low total bilirubin difference of that day is probably a combined effect of ineffective treatment and sufficient hemofiltration. However, even the short treatment time allowed bilirubin separation as well as separation of hydrophilic uremic toxins like urea, creatinine or ammonia (due to the second dialyzer enclosed in the dialysate circuit).

Tab. 14. Patient 2: Total bilirubin levels pre- and post-treatment

| No. of treatment | time of treatment (h) | Total serum bilirubin | | Total decrease (mg/dl) |
|---|---|---|---|---|
| | | before treatment (mg/dl) | after treatment (mg/dl) | |
| 1 | 4 | 37.7 | 32.2 | 5.5 |
| 2 | 5 | 37.0 | 29.1 | 7.9 |
| 3 | 4 | 32.4 | 27.5 | 4.9 |
| 4 (MARS + HDF) | 2°2 | 32.8 | 32.1 | 0.7 |
| 5 | 4 | 32.4 | 28.5 | 3.9 |

Tab. 15. Patient 2: Serum urea and creatinine levels pre- and post-treatment

| No of treatment | time of treatment | Urea (mg/dl) | | Creatinine | |
|---|---|---|---|---|---|
| | | before treatment | after treatment | before treatment | after treatment |
| 1 | 4 | 160 | 138 | 3.9 | 3.1 |
| 2 | 5 | 194 | 153 | 4.1 | 3.4 |
| 3 | 4 | 208 | 152 | 4.7 | 3.6 |
| 4 (Mars + HDF) | 2 + 2 | 226 | 136 | 5.2 | 3.1 |
| 5 | 4 | 202 | 148 | 4.9 | 3.7 |

Patient 3 female, 29 years old, chronic alcoholic liver insufficiency

The patient had a long history of alcohol abuse with a known chronic liver insufficiency that was clinically estimated to be on a precirrhotic level. Admittance happened upon increasing jaundice and worsening of the general status. Under conventional treatment the patient went into hepatic encephalopathy grade IV, i.e. she fell into deep coma and did not respond to painful stimuli. Bilirubin levels rose to 29,5 mg/100 ml. She showed life-threatening severe acid-base disturbances, pulmonary edema, hypoxemia on the first day of MARS- treatment and was estimated moribund by experienced medical doctors. In this status treatment with the method according to the present invention was started as ultima ratio. Within two days the severe life-threatening status totally changed into a moderate state of disease with normal acid-base values, normooxygenation and normal ventilation. The patient awoke from coma and went back to encephalopathy grade I/II, i.e. she reacted adequately although with a slurred speech. The patient was treated for six consecutive days for six hours per day. The bilirubin level continuously decreased to 16,2 mg/100 ml during this time.

Tab. 16. Patient 3: Total serum bilirubin levels pre- and post-treatment during 4 MARS sessions (1–4) and two hemodiafiltration sessions (5–6)

| No. of treatment | time of treatment (h) | Total serum bilirubin | | Total decrease (mg/dl) |
|---|---|---|---|---|
| | | before treatment (mg/dl) | after treatment (mg/dl) | |
| 1 | 5 | 29.0 | 24.3 | 4.7 |
| 2 | 6 | 26.9 | 19.9 | 7.0 |
| 3 | 5 | 23.4 | 17.8 | 5.6 |
| 4 | 5 | 18.3 | 13.1 | 5.2 |
| 5 | 5 | 15.9 | 12.9 | 3.0 |
| 6 | 4.5 | 16.5 | 15.6 | 0.9 |

Patient 4 female, 41 years old, digoxin intoxication

The patient showed typical clinical signs of digoxin intoxication such as tachyarrhytmia, loss of appetite, vomitting, diarrhoea; ECG showed ventricular arrhythmia and typical ST-changes. After four hours of treatment the clinical symptoms normalized completely and so did the ECG changes.

Tab. 16 shows single pass clearances at the start and at the end of the treatment. A highly toxic starting level and sufficient regeneration of digoxin by on line-adsorption/dialysis in the closed-loop liquid (B) dialysate circuit (3,95 to 0,5 and 2,55 to 0,54) were noted. No saturation of the liquid (B) dialysate circuit and the adsorbents (PBS) was recognized. Since digoxin is distributed in many tissues the blood level normally decreases very slowly because of continuous influx from the other tissues. Therefore a longer treatment, ideally a continuous one, would be desirable.

Tab. 17. Patient 4: Single pass clearances of digoxin during 4 hours of MARS

| time | location | digoxin | |
|---|---|---|---|
| | | serum concentration (µmol/l) | dialysate concentration (µmol/l) |
| start | pre dialyzer | 7.45 | 0.50 |
| | post dialyzer | 3.66 | 3.95 |
| end | pre dialyzer | 5.84 | 0.54 |
| | post dialyzer | 3.86 | 2.55 |

The above is intended to illustrate the present invention but is not limiting. Numerous variations and modifications can be effected without departing from the spirit and scope of the novel concepts of the invention. It is to be understood that no limitation with respect to the specific compositions and uses described herein is intended or should be inferred.

What is claimed is:

1. A process of separating substances bound to a first protein in a first liquid by means of a semipermeable membrane separating the first liquid from a second liquid, the process comprising the steps of:

a) impregnating the membrane by passing a solution along both sides of the membrane, the solution containing the first protein, which first protein has an acceptor function for the substances to be separated and an affinity for the membrane, for a period of time sufficient to permit penetration and adsorption of the first protein on both sides of the membrane; and b) passing the first liquid and the second liquid on each side of said semipermeable membrane, the second liquid containing the first protein in free form, wherein the membrane contains (i) a first structure facing the first liquid and having tunnels with a length of 0.01 to 0.1 micrometer and a diameter that permits passage of the substances to be separated but excludes passage of the first protein and (ii) a port- and adsorption structure facing the second liquid that permits the second liquid and the first protein therein to pass into and out of the port- and adsorption structure, whereby the substances bound to the first protein in the first liquid are separated from the first protein and passed through the membrane to the first protein in the second liquid.

2. The process of claim 1 wherein membrane material is selected from the group consisting of polysulfones, polyamides, polycarbonates, polyesters, acrylonitrile polymers, vinyl alcohol polymers, acrylate polymers, methacrylate polymers and cellulose acetate polymers.

3. The process of claim 2 wherein the membrane material is polysulfone.

4. The process of claim 1 wherein the first liquid is plasma or blood and the second liquid comprises human serum albumin as a protein having an acceptor function for the protein-bound substances.

5. The process of claim 4 wherein the first protein is human serum albumin.

6. The process of claim 1 wherein the second liquid comprises human serum albumin.

7. The process of claim 6 wherein the human serum albumin is in a concentration from about 6 to about 40 grams per 100 ml.

8. The process of claim 6 wherein the human serum albumin is in a concentration from about 8 to about 30 grams per 100 ml.

9. The process of claim 6 wherein the human serum albumin is in a concentration from about 8 to about 20 grams per 100 ml.

10. The process of claim 1 wherein the second liquid is transported with an alternating influx and outflux movement in a direction perpendicular to an outer membrane surface such that the second liquid moves into and out of the port- and adsorption structure.

11. The process of claim 1 wherein impregnating is accomplished at a temperature of from about 15° C. to about 40° C., a pH of from about 5 to about 9 and for a time from about 1 to about 120 minutes.

* * * * *